US008568790B2

(12) United States Patent
Moloney

(10) Patent No.: US 8,568,790 B2
(45) Date of Patent: Oct. 29, 2013

(54) MEDICINAL COMPOSITIONS CONTAINING HONEY

(75) Inventor: Anthony Peter Moloney, Mt Cotton (AU)

(73) Assignee: Medihoney Pty Ltd., Queensland (AU)

( * ) Notice: Subject to any disclaimer, the term of this patent is extended or adjusted under 35 U.S.C. 154(b) by 669 days.

(21) Appl. No.: 12/301,931

(22) PCT Filed: May 31, 2007

(86) PCT No.: PCT/AU2007/000771

§ 371 (c)(1), (2), (4) Date: Feb. 4, 2009

(87) PCT Pub. No.: WO2007/137369

PCT Pub. Date: Dec. 6, 2007

(65) Prior Publication Data

US 2010/0233283 A1 Sep. 16, 2010

Related U.S. Application Data

(60) Provisional application No. 60/809,489, filed on May 31, 2006.

(51) Int. Cl.
*A61K 35/24* (2006.01)
*A61K 35/37* (2006.01)
*A61K 31/74* (2006.01)
*A61K 36/00* (2006.01)

(52) U.S. Cl.
USPC ........ 424/537; 424/78.04; 424/725; 424/778; 514/912

(58) Field of Classification Search
None
See application file for complete search history.

(56) References Cited

U.S. PATENT DOCUMENTS

| | | | |
|---|---|---|---|
| 5,889,015 A | 3/1999 | Sequeira et al. | |
| 6,956,144 B2 * | 10/2005 | Molan | 602/48 |

FOREIGN PATENT DOCUMENTS

| | | |
|---|---|---|
| GB | 2 391 809 A | 2/2004 |
| NZ | 502158 | 5/2002 |
| WO | WO 01/67888 | 9/2001 |
| WO | WO 2005/120250 | 12/2005 |
| WO | WO 2007/009185 | 1/2007 |

OTHER PUBLICATIONS

Lusby, P.E., Coombes, A.L., and Wilkinson, J.M. (2005) Bactericidal Activity of Different Honeys against Pathogenic Bacterial. Archives of Medical Research 36; pp. 464-467.*

McGee, H. (2004) On Food and Cooking: The Science and Lore of the Kitchen (2nd Ed. Schribner, New York, NY) pp. 666.*

Cooper, R.A. et al. "Antibacterial activity of honey against strains of *Staphylococcus aureus* from infected wounds." Journal of the Royal Society of Medicine, vol. 92, (6) (1999), pp. 283-285.

Willix, D.J. et al. "A comparison of the sensitivity of wound-infecting species of bacteria to the antibacterial activity of manuka honey and other honey." Journal of Applied Bacteriology vol. 73 (5) (1992), pp. 388-394.

Snow, M.J. et al. "On the nature of non-peroxide antibacterial activity in New Zealand manuka honey." Food Chemistry, vol. 84 (1) (2004), pp. 145-147.

Lusby, P.E. et al. "Honey: A Potent Agent for Wound Healing?" Journal of Wound, Ostomy and Continence Nursing, vol. 29 (6) (2002), pp. 295-300.

Allen, K.L. et al. "A Survey of the Antibacterial Activity of Some New Zealand Honeys," Journal of Pharmacy and Pharmacology, vol. 43, (12) (1991), pp. 817-822.

The International Search Report in corresponding PCT Application No. PCT/AU2007/000771.

Aljadi et al., "Isolation and identification of phenolic acids in Malaysian honey with antibacterial properties", *Turk J Med Sci* (2003) 33:229-236.

Al-Waili, N., "Intrapulmonary Administration of Natural Honey Solution, Hyperosmolar Dextrose or Hypoosmolar Distill Water to Normal Individuals and to Patients with Type-2 Diabetes Mellitus or Hypertension: Their Effects on Blood Glucose Level, Plasma Insulin and C-Peptide, Blood Pressure and Peaked Expiratory Flow Rate", *Eur J Med Res* (2003) 8: 295-303.

Al-Waili, Noori S., Intravenous and Intrapulmonary Administration of Honey Solution to Healthy Sheep: Effects on Blood Sugar, Renal and Liver Function Tests, Bone Marrow Function, *J. of Medicinal Food* (2003) 6(3): 231-247.

Al-Waili, Noori S., "Investigating the antimicrobial activity of natural honey and its effects on the pathogenic bacterial infections of surgical wounds and conjunctiva" *J Med Food* (2004) 7(2): 210-222.

Dutka-Malen, et al., "Detection of Glycopeptide Resistance Genotypes and Identification to the Species Level of Clinically Relevant Enterococci by PCR" *J. of Clinical Microbiology* (1995) 33(1): 24-27.

Emarah, Mohamed H., "A clinical study of the topical use of bee honey in the treatment of some ocular diseases" *Bulletin of Islamic Medicine* (1982) 2(5): 422-425.

Gendrolis, et al., "Bee products for treatment of diseases of mouth and upper respiratory tract" *Medicina* (Kaunas) (2004) 40(8): 770 (Summary Only).

Lemp, Michael A., "Tear film, pharmacology of eye drops, and toxicity" *Current Opinion in Ophthalmology* (1993) 4(IV): 14-19.

Mansour, Ahmad M., "Letter to the Editor: Epithelial corneal oedema treated with honey" *Clinical and Experimental Ophthalmology* (2002) 30: 149-150.

Molan, P.C., "Honey as an Antimicrobial Agent" in *Bee Products: Properties, Applications, and Apitherapy*, Mizrahi, A. and Yaacov Lensky, 1997, Springer.

Mwai, et al., "Decisions in Global Sourcing and Supply: Deep Red Canning Co." *International Food and Agribusiness Management Review* (2005) 8(1): 102-113.

Wikler, et al., Methods for Dilution Antimicrobial Susceptibility Tests for Bacteria That Grow Aerobically; Approved Standard—Eighth Edition, vol. 29, No. 2 (2009).

"Honey's source kept secret", *NZ Beekeeper* (1998): 27.

(Continued)

*Primary Examiner* — Chris R Tate
*Assistant Examiner* — Russell Fiebig
(74) *Attorney, Agent, or Firm* — Marc T. Morley

(57) ABSTRACT

The present invention relates to medicinal compositions containing a honey having non peroxide antibacterial activity and wherein the composition comprises from about 19% to about 80% water by weight. The use of these compositions in the treatment of eye, respiratory and ear conditions is also disclosed.

14 Claims, No Drawings

(56) References Cited

OTHER PUBLICATIONS

*Dry Eye Syndrome*, P&T Digest, John D. Sheppard, MD, MMSc, Chief Medical Editor, 12(12):1-45 (2003).
*The Hive and the Honey Bee*, Ed. By J.M. Graham, Revised Edition, 2000, Hamilton, Illinois, Dadant and Sons, Inc., pp. 900-903.
Cough Remedies—Health 911, http://web.archive.org/web/20041229-20040127re_/ http://www.health911.com/remedies/rem_coughs.html, pp. 1-5 (last visited May 7, 2010).
Filtering honey [Archive]—Beesource Beekeeping Forums, http://www.beesource.com/forums/archive/index.php/t-206782.html, pp. 1-2 (last visited May 7, 2010).
Health Benefits of Honey, http://web.archive.org/20051231-re_ http://www.benefits-of-honey.com/health-benefits-of-honey.html, pp. 1-4 (last visited Jun. 24, 2010).
Kissell, Honey as Medicine Sweet Relief, http://itotd.com/articles/218/honey-as-medicine/, Jun. 17, 2004.
Manuka Honey USA Customer Testimonies, http://web.archive.org/web/19960101000000-20091202220343/http://www.manukahoneyusa.com/CustomerTestimonies.html, pp. 1-4 (last visited Jun. 24, 2010).
Bang, et al., "The Effect of Dilution on the Rate of Hydrogen Peroxide Production in Honey and Its Implications for Wound Healing" *The Journal of Alternative and Complementary Medicine* (2003) 9(2): 267-273.
Bansal, et al., "Honey—A remedy rediscovered and its therapeutic utility" *Kathmandu U. Med. J.* (2005) 3(3): 305-309.
Cooper, et al., "Antibacterial activity of honey against strains of *Staphylococcus aureus* from infected wounds" *J. of the Royal Society of Med.* (1999) 92: 283-285.
Cooper, et al., "The Efficacy of Honey in Inhibiting Strains of *Pseudomonas aeruginosa* From Infected Burns" *J. Burn Care & Rehabilitation* (2002) 23(6): 366-370.
Cooper, et al., "Susceptibility of multiresistant strains of *Burkholderia cepacia* to honey" *Letters in Applied Microbiology* (2000) 31: 20-24.
Cooper, R.A., "Medical Manuka Honey, Chapter 2: The Antimicrobial Activity of Honey" *Advancis Medical*, Kirkby-in-Ashfield, Nottinhamshire, UK, Apr. 5, 2005, Retrieved from the Internet: http://www.medicalhoney.com/downloads/_pdfs/chapter_2.pdf (retrieved on May 18, 2012).
Davis, C., *The Use of Australian Honey in Moist Wound Management*, RIRDC Web Publication No. W05/159 (2005).
Molan, P.C., "Why honey is effective as a mediine: 1) Its use in modern medicine" *Bee World* (1999) 80(2): 80-92.
Molan, P.C., "Why honey is effective as a mediine: 2) The scientific explanation of its effects" *Bee World* (2001) 82(1): 22-40.
Molan, P.C., *Honey as a topical antibacterial agent for treatment of infected wounds*, World Wide Wounds (2001) http://www.worldwidewounds.com/2001/November/molan/honey-as-topical-agent.html.
Prescott, Harley and Klein, *Microbiology* 5th Ed., McGraw-Hill (2002) pp. 121-123.
Yoon, Young Mee and Claire Newlands, "Quality Standards of Medical Grade Manuka Honey" in White R., Cooper R. eds. *Honey: A Modern Wound Management Productl*, Aberdeen, UK (2005) pp. 89-102.
Zumla, et al., "Honey—A remedy rediscovered" *J. of the Royal Society of Med.* (1989) 82: 384-385.
Specification of expired provisional application of New Zealand Patent No. 547946.
Specification of pending patent application of New Zealand Patent No. 547946.

* cited by examiner

MEDICINAL COMPOSITIONS CONTAINING HONEY

This application is U.S. National Phase of International Application PCT/AU2007/000771, filed May 31, 2007, which designated the United States and was published in English, which claims priority to U.S. Provisional Application No. 60/809,489, filed May 31, 2006, the entire contents of which are incorporated herein by reference.

FIELD OF THE INVENTION

The invention generally relates to medicinal compositions containing honey solutions and their use in treating ophthalmic, respiratory and ear conditions.

BACKGROUND OF THE INVENTION

People have known for thousands of years that raw honey has many medicinal properties such as wound healing and antibacterial activity. Honey was widely used for medicinal purposes in the ancient world and is still common in Africa, India and the Middle East. However, despite extensive research, the healing properties of honey have not yet been fully elucidated.

Most honeys are in some way antibacterial, some more than others. Honey with high antibacterial activity, typically has high levels of hydrogen peroxide ($H_2O_2$) which is referred to as "peroxide activity" (PA). Other properties of honey commonly known to underpin its antibacterial activity are low pH and high sugar content (high osmotic effect). It is likely that the historical use of honey as a wound healing agent stems from its antibacterial activity.

The PA activity of honey is derived from an enzyme called glucose oxidase. Like many enzymes, glucose oxidase is inactivated by light and heat. The stronger the light and/or heat, the faster it is inactivated. Room temperature and low light, given enough time, will also reduce the glucose oxidase activity. Glucose oxidase only becomes active when honey is diluted. The precise reasons for the activation of the enzyme upon dilution are still not clearly known.

Two honeys, known as jelly bush and manuka honey, are interesting because they can have anti-microbial activity due to some property other than the production of hydrogen peroxide, low pH or high sugar content. Both jelly bush and manuka are plants that are *Leptospermum* species. The antibacterial activity of these honeys is referred to as the non-peroxide activity (NPA). Unlike PA, NPA is stable to moderate heat, light and even gamma radiation.

Honey is a complex, naturally occurring, mixture of components. After processing of the collected nectar by bees (including addition of various components one of the most important of which is diastase), the water content of the modified nectar evaporates slowly from about 70 to 80% by weight, to about 17 to 18% by weight, eventually providing ripe honey. Ripe honey, therefore, has a low water activity, which contributes to its high osmotic effect and therefore its antibacterial activity. However upon dilution, honey is susceptible to fermentation, typically because of the presence of the ubiquitous yeasts such as *zygosaccharomyces rouxii*.

Honey has previously been used to treat a wide range of indications. For example, Al-Waili (Al-Waili N. S., *J Medicinal Food,* 2004, 7(2), 210-222) reported on the effect of unadulterated honey on bacterial conjunctivitis, induced in mice, compared to appropriate antibiotics, oflaxocin and chloramphenicol. Better outcomes on bacterial conjunctivitis, such as reduced redness, swelling and eradication of bacterial infection, using honey compared to oflaxocin or chloramphenicol eye drops or control (no intervention) were observed.

The use of unadulterated honey in treating other ocular disorders has also been reported. Mansour (Mansour A. M., *Clinical and Experimental Ophthalmology,* 2002; 30: 149-150) reported the use of topical honey on 16 consecutive patients with corneal oedema. Epithelial oedema was immediately cleared in all corneas, improving visual acuity, and decreasing pain associated with bullous keratopathy. Initial application of honey caused a stinging sensation but its effect was short lasting. In addition, Emarah (Emarah M. H., Bulletin of Islamic Medicine, 1982, 2(5), 422-425) treated 102 patients, with various ocular diseases not responding to conventional treatment, with unadulterated honey by application to the conjunctival sac. Greater than 80% of patients improved with the honey treatment and no patient got worse with this treatment. A transient stinging sensation and redness of the eye was reported but was not severe.

Direct application of unadulterated honey to, for example, a site of injury, can be difficult because of honey's inherent properties such as varying viscosity and natural "stickiness". Use of unadulterated honey can also be time consuming, messy and impractical. The problems associated with the application of honey may result, for example, in low patient compliance.

The present invention arises from the unexpected discovery that honey having non-peroxide antibacterial activity, for example honey derived from *Leptospermum* species, may be diluted to have a water content at which honey would be normally expected to undergo bacterial spoilage. Further, the dilute honey may be filtered in a more facile manner and has a reduced stinging sensation when applied to the eyes over undiluted honey. The diluted honey retains significant antibacterial properties and in addition to its other beneficial properties has a shelf life.

SUMMARY OF THE INVENTION

Accordingly, the present invention relates to the medicinal properties of honey having non-peroxide antibacterial activity such as honey substantially derived from *Leptospermum* species, to the use of this honey in medicinal compositions such as ophthalmic, respiratory or otic compositions, to the compositions themselves, and to the various applications of those compositions in the treatment of ophthalmic, respiratory or ear conditions.

Thus, in one aspect, the present invention provides a medicinal composition comprising a honey having non-peroxide antibacterial activity, wherein the composition comprises from about 19% to about 80% water by weight.

In some embodiments, the composition comprises less than 65% water by weight and in other embodiments less than 50% water by weight. In some embodiments, the composition comprises less than 30% water by weight and in other embodiments, less than 27% water by weight. In one embodiment, the composition comprises about 25% water by weight.

Suitably, the medicinal composition comprises a water activity from about 0.63 to about 0.85.

Suitably, the medicinal composition has been filtered to remove particles of greater than about 25 microns. In some embodiments, the composition has been filtered to remove particles of greater than about 10 microns, and in further embodiments the composition has been filtered to remove particles of greater than about 5 microns.

In some embodiments, the medicinal composition comprises an ancillary pharmaceutically active agent.

The invention in another aspect, is directed to the use of a composition comprising a honey having non-peroxide antibacterial activity, wherein the composition comprises from about 19% to about 80% water by weight, in the manufacture of a medicament for treating ophthalmic, respiratory or ear conditions.

In yet another aspect, the invention provides for the use of an medicinal composition comprising honey having non-peroxide antibacterial activity, wherein the composition comprises from about 19% to about 80% water by weight, for the treatment of ophthalmic, respiratory or ear conditions.

In still another aspect, the invention provides a method of treating an ophthalmic, respiratory or ear condition in a subject, the method comprising administering to the subject a therapeutically effective amount of a medicinal composition comprising a honey having non-peroxide antibacterial activity, wherein the composition comprises from about 19% to about 80% water by weight. In specific embodiments, the composition is applied topically.

DETAILED DESCRIPTION OF THE INVENTION

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

As used herein the term "blepharitis" refers to an abnormal condition wherein tears contain an excess of lipids (the oily ingredient in natural tears) and, in some cases, contain an irritating oil as well. Under normal conditions, the lipids in tears serve to prevent evaporation of the aqueous layer that wets the corneal epithelium of the eye and helps spread the aqueous layer over the normally aqueous-resistant cornea during a blink. If excess oil or lipid is present, the lipid layer will tend to adhere to the cornea itself. If the eye is unable to clear this oil from the surface of the cornea, a "dry" area occurs on the cornea since the aqueous layer is unable to hydrate this area.

Throughout this specification and the claims which follow, unless the context requires otherwise, the word "comprise", or variations such as "comprises" and "comprising", will be understood to imply the inclusion of a stated integer or step or group of integers or steps but not the exclusion of any other integer or step or group of integers or steps.

As used herein the term "condition" refers to an abnormality in the physical state of the body as a whole or one of its parts. For example "disease" refers to a pathological condition of a part, organ, or system of an organism resulting from various causes, such as infection, genetic defect, or environmental stress, and is typically characterised by an identifiable group of signs or symptoms As defined herein, the term "conjunctivitis" refers to inflammation of conjunctiva or membrane that covers the white of the eye and inner surfaces of the eyelid. Conjunctivitis is typically characterised by discharge, grittiness, redness and swelling. Conjunctivitis may result from virus, bacteria, allergens, chemical exposure or ultraviolet light exposure and, depending on cause, may be contagious.

The term "dilution", as used herein, generally encompasses the ordinary meaning of that term, namely, the reduction in the amount of a particular subject material per unit volume of a fluid containing that material, through the addition of a second fluid, or diluent, to a first fluid which contains the subject material, e.g., soluble chemical component, or a suspension or emulsion of a partially insoluble material, whereby the resulting concentration of the subject material is reduced over that of the first fluid. In terms of the present invention, the diluent may take on a variety of forms, including aqueous or non-aqueous fluids and/or it may include additional material components.

A used herein the term "disease" refers to any abnormal condition of the body or mind that causes discomfort, dysfunction, or distress to the person affected or those in contact with the person. Sometimes the term "disease" is used broadly to include injuries, disabilities, syndromes, symptoms, deviant behaviours, and atypical variations of structure and function, while in other contexts these may be considered distinguishable categories.

As herein used, the term "disorder" refers to any deviation from the normal structure or function of any part, organ, or system of the body that is manifested by a characteristic set of symptoms and signs whose pathology and prognosis may be known or unknown.

As used herein, the term "dry eye" or variations such as dry eye syndrome" (technically known as keratoconjunctivitis (KCS)) is defined as the condition where the tear quantity has been decreased or tear quality has become abnormal. Dry eye syndrome has been associated with, for example: hypolacrimation; alacrima; xerophthalmia; Sjögren's syndrome; dry keratoconjunctivitis; Stevens-Johnson syndrome; ocular pemphigoid; marginal blepharitis; diabetes; surgery for cataract; allergic conjunctivitis; hypolacrimation due to increased VDT (visual display terminal) tasks or dry air in an air-conditioned room. "Dry eye" may occur because of a diminution of the quantity of tears produced and distributed through the lacrymal ducts, as well as because of a decrease in the stability of the tear film produced. "Dry eye" acts to decrease visual acuity; produces discomfort; and eventually, if allowed to remain untreated and uncorrected, may result in permanent damage with degradation of the exposed ocular tissues, a complete breakdown of corneal tissue necessitating, in the extreme, corneal transplants.

As used herein, the term "ear conditions" refers to infections of the ear, for example, external otitis (infection of the ear canal), acute otitis media (bacterial or viral infection of the middle ear often secondary to an upper respiratory tract infection) and chronic otitis media.

The term "floral source" as used herein, refers to the flower, or flowers of a botanical specie(s) from which the bees have gathered the nectar to make honey. For example, unifloral source refers to a source which is a single botanical species.

The term "Fuchs' dystrophy" as used herein, refers to the gradual deterioration of endothelial cells for no apparent reason. As these cells thin over time, the cornea is less capable of removing water form the stroma, causing it to swell and distort vision. Haze and small blisters on the corneal surface may also appear. Fuchs' dystrophy, may alternatively be described as a dystrophy of the posterior cornea (endothelial) that is characterised by a progressive de-compensation of the endothelium associated with a variable degree of nodular thickening of Descemet's membrane.

As used herein, the term "graft-versus-host disease" (GVHD) refers to a condition where following transplantation the donor's immune cells in the transplant (graft) make antibodies against the patient's tissues (host) and attack vital organs. Organs most often affected include the eyes, skin, gastrointestinal (GI) tract and the liver. A high proportion of bone marrow transplants lead to GVHD. Solid organ transplantation, blood transfusions, and maternal-fetal transfusions have also been reported to cause GVHD less frequently.

The term "gum", as used herein, refers to any synthetic polymer, natural polysaccharide, or derivatised natural polysaccharide that is ophthalmically compatible and that increases the viscosity of a solution sufficiently to increase the viscosity of the solution in which it is found or to transform a drop of the solution into a semi-solid or gelatinous state after administration to an eye of a warm-blooded mammal. Examples of synthetic polymer gums include, but are not limited to, polyethylene glycol, polyvinyl pyrrolidone, carboxymethyl cellulose, polyvinyl alcohol and derivatives thereof, and Carbopol and derivatives thereof. Examples of natural polysaccharide gums include, but are not limited to, carrageenan, konjac, sodium alginate, aloe vera gel, agarose, guar, pectin, tragacanth, acacia, Arabic, curdlan, gellan, xanthan, scleroglucan, hyaluronic acid, or chitosan. Examples of derivatised natural polysaccharide gums include, but are not limited to, propyleneglycol alginate and hydroxypropyl guar.

By the term "honey" is meant a sweet and viscous fluid produced by honeybees and other insects from the nectar of flowers. In general, pure, ripe honey, does not include added substances such as water or other sweeteners. Typically, pure, ripe honey does not spoil as natural airborne yeasts cannot become active in it because the moisture content is too low. Natural, raw honey typically varies from 14% to 18% moisture content by weight. As long as the moisture content remains under 18% by weight, virtually no organism can successfully multiply to significant amounts in honey. The study of pollens and spores in raw honey (melissopalynology) can determine floral sources of honey. By referring to honey as "unadulterated honey" or "pure honey", it is meant "ripe honey" that has not been modified by the further addition of any substance including those substances which are known to occur naturally in honey. By "ripe honey", it is meant honey naturally produced by bees to have a water content, in a range known to those skilled in the art, which typically varies from about 14% to about 18% water by weight.

The term "honey having non-peroxide antibacterial activity" refers to a honey that retains its antimicrobial activity in the absence of the production of hydrogen peroxide. Suitable honeys include those substantially derived from plants of the *Leptospermum* sp. such as *Leptospermum scoparium, Leptospermum polygalifolium, Leptospermum semibaccatum, Leptospermum semibaccutum, Leptospermum trinervium, Leptospermum whitei, Leptospermum speciosum* and *Leptospermum liversidgei.*

By the phrase "honey substantially derived form a *Leptospermum* sp." is meant a honey that is produced from nectar, at least about 50%, for example 75%, 85%, 95% or 98%, of which is derived from one or more Leptospermum species.

As used herein, the term "keratitis" refers to a medical condition of the eye in which the cornea is inflamed. Keratitis is often characterised by cloudiness or loss of luster. There are many types, causes and degrees of severity. Bacterial infection of the cornea can follow from an injury or from contact lens wearing. Viral infection of the cornea is usually caused by a herpes virus and is called a dendritic ulcer due to its shape when looked at with a slit lamp. Amoebic infection of the cornea is the most serious corneal infection, usually only affecting soft contact-lens wearers.

As used herein, the term "*Leptospermum* sp." refers to a genus of plants in the myrtle family Myrtaceae and includes *Leptospermum scoparium, Leptospermum polygalifolium, Leptospermum semibaccatum, Leptospermum semibaccutum, Leptospermum trinervium, Leptospermum whitei, Leptospermum speciosum* and *Leptospermum liversidgei.*

As used herein the term "moisture" essentially refers to water, quantitatively (and sometimes qualitatively) determined by definite prescribed methods which may vary according to the nature of the material.

As used herein, the term "ophthalmic condition" refers to any disease, condition or disorder of the eye.

The term "microbial infection" as used herein refers to any pathological presence on or in an injury or insult to a any organ of a human or animal. It is further understood that a "microbial infection" may include any systemic infection that is amenable to inhibition by application of an antimicrobial composition.

The term "ophthalmically acceptable" with respect to a composition, solution or component thereof, herein means having no persistent detrimental effect on the treated eye or the functioning thereof, or on the general health of the subject being treated. It will be recognised that transient effects such as minor irritation or a "stinging" sensation are common with topical ophthalmic administration, and the existence of such transient effects is not inconsistent with the formulation, composition or ingredient in question being "ophthalmically acceptable" as herein defined. However, preferred compositions, solutions and components thereof, are those that cause little or no substantial detrimental effect, even of a transient nature.

As used herein the term "polysaccharide" refers to any of a class of carbohydrates consisting of chains of monosaccharides. Polysaccharides can be naturally-occurring (typically of algal, botanical, mammalian or microbial origin (fungal, yeast, bacterial, etc.)), synthetic or semisynthetic. Polysaccharides are classified on the basis of their main monosaccharide components and the sequences and linkages between them, as well as the anomeric configuration of linkages, the ring size (furanose or pyranose), the absolute configuration (D- or L-) and any other substituents present. Certain structural characteristics such as chain conformation and intermolecular associations will influence the physico-chemical properties of polysaccharides. The hydrodynamic volumes (and hence viscosities) of more-extended well-hydrated polysaccharides, (such as for example, alginates and xanthans) increase approximately linearly with molecular weight.

As used herein, the term "respiratory condition" refers to any disease, condition or disorder of the respiratory tract. As used herein, the "respiratory tract" includes the nose, nasal passages, paranasal sinuses, throat or pharynx, voice box or larynx, trachea, bronchi, bronchioles and lungs including the respiratory bronchioles, alveolar ducts, alveolar sacs and alveoli. Suitable respiratory conditions that may be treated or prevented with the composition of the invention include, but are not limited to, lung and bronchopulmonary infections including those caused by *Pseudomas aeruginosa, Pneumocystis carinii, Staphylococcus aureus, Haemophilus influenzae, Mycobacterium tuberculosis, Mycobacterium bovis, Mycobacterium africanum, Mycobacterium canetti* and *Mycobacterium microti*; and infections associated with cystic fibrosis, tuberculosis and AIDS, sinusitis, acute rhinitis, atrophic rhinitis, pharyngitis, tonsillitis, laryngitis and bacterial infections of the nasal cavity, for example those due to *Klebsiella ozenae* and nosocomial *S. aureus* bacteraemia due to nasal carrier.

As used herein the term "Sjogrens's syndrome" refers to an autoimmune disease that classically combines dry eyes, dry mouth, and another disease of the connective tissues such as rheumatoid arthritis, lupus, scleroderma or polymytosis. With "Sjogrens's syndrome", inflammation of the glands that produce tears (the lacrimal glands) leads to decreased tears and dry eyes, and inflammation of the glands that produce the saliva in the mouth (salivary glands, including the parotid glands) leads to dry mouth. Sjogren's syndrome can consequently be complicated by infections of the eyes, breathing passages including the nose, and mouth. About 90% of people with Sjogren's syndrome are female, usually in middle age or beyond. Sjogren's syndrome is typically associated with auto-antibodies, antibodies produced by the body that are directed against a variety of body tissues. Aqueous tear deficiency may be subclassified into non-Sjogren's syndrome and Sjogren's syndrome groups. Patients with non-Sjogren's aqueous tear deficiency have less-severe symptoms and ocular surface disease than those with Sjogren's syndrome. The etiology of non-Sjogren's aqueous tear deficiency has not been established, but it appears to be multifactorial.

By the term "substantially" is meant at least about 50%, for example 75%, 85%, 95% or 98%.

As used herein the term "tear" refers to a liquid produced by lacrimation, for cleaning and lubricating the eyes. Lacrimation is a mammal's process of producing tears. The word lacrimation may also be used in a medical or literary sense to refer to crying. Tears are composed of three layers, aqueous, mucin and lipid layers. The mucin layer adheres to the corneal surface, which surface would repel water without the mucin in place. The aqueous layer then provides wetting of the corneal epithelium by adhering or spreading over the mucin. The outer lipid or oily layer prevents evaporation of the aqueous layer (without the lipid layer, tears would evaporate 10 to 20 times faster) and helps spread the aqueous layer during a blink. When the lipid layer adheres to the mucin layer, or to the cornea itself, rapid tear breakup occurs. If the eye is unable to clear this oil off the surface, a dry area occurs on the cornea as the aqueous material cannot hydrate it.

As used herein the term "tear secretion" refers to the secretion of a liquid produced by lacrimation. The term "tear secretion" may be further classified as (1) basal tear secretion, (2) reflex tear secretion and (3) crying or weeping tear secretion. In healthy mammalian eyes, the cornea is continually kept wet and nourished by basal tears. They lubricate the eye and help to keep it clear of dust. Tear fluid contains water, music, lipids, lysozyme, lactoferrin, lipocalin, immunoglobulins, glucose, urea, sodium and potassium. Some of the substances in lacrimal fluid fight against bacterial as a part of the immune system. The second type of tear results from irritation to the eye by foreign particles, or substances such as onion vapours, tear gas or pepper spray. These reflex tears attempt to wash out irritants that may have gotten into the eye. The third category, also referred to as crying or weeping, is increased lacrimation due to strong emotional stress or pain. This practice is not restricted to negative emotions; many people have been known to cry when extremely happy. In humans, emotional tears can be accompanied by reddening of the face and sobbing—cough-like, convulsive breathing, sometimes involving spasms of the whole upper body. Tears brought about by emotions have a different chemical make up than those for lubrication.

The term "therapeutically effective", with reference to an amount or dosage of a composition of the present invention, refers to an amount of a composition which is sufficient to effectively treat a disorder or condition requiring treatment.

As used herein, the term "treatment" or "treating" refers to any means of control of a condition or disorder, including prevention or prophylaxis, cure and relief, or arrestation or relief of development of the condition or disorder.

As used herein the term "water activity" ($a_w$) refers to a measure of the free moisture in a substance and is the quotient of the water vapour pressure of the substance divided by the vapour pressure of pure water at the same temperature. Water activity is expressed as a scale from 0.0 (bone dry) to 1.0 (pure water). The value of water activity is different than the moisture content (% water). The moisture content is the total moisture, that is, the amount of bound plus free water present in a substance. Water activity is specific, it provides a measurement of the free moisture and is usually expressed as "$a_w$" or a percentage (%).

As used herein, a "wetting agent" refers to a compound that modifies the characteristics between phases, such as liquid—liquid phases, or solid—liquid phases, to promote contact between phase surfaces. As such a "wetting agent" is a material that increases the spreading of a liquid medium on a surface by reducing the surface tension of the liquid. A wetting agent may be a material which lowers the interfacial tension between a liquid and a solid. When a wetting agent reduces surface tension, spreading naturally occurs. Wetting agents may be designed specifically for use with a particular ophthalmic composition. Suitable wetting agent are, for example, polysaccharides such as chitosans.

As mentioned, ripe honey will not ferment and may therefore be readily stored. Honey with less than 17.1 percent water will not ferment in a year, irrespective of the yeast count. Between 17.1 and 18 percent moisture, most honeys with 1,000 yeast spores or less per gram will be safe for a year. When moisture is between 18.1 and 19 percent, not more than 10 yeast spores per gram can be present for safe storage. Above 19 percent water, most honeys can be expected to ferment even with only one spore per gram of honey, a level so low as to be very rare ("The Hive and the Honey Bee" Edited by J. M. Graham, Revised Edition, 2000, Hamilton, Ill., Dadant and Sons, Inc).

The inventors have surprisingly found that honeys having non-peroxide antibacterial activity such as those substantially derived from the *Leptospermum* species, may be diluted to greater than 19% water by weight whilst remaining unsusceptible to fermentation. Furthermore, it was found that an aqueous dilution of these honeys provides a composition that is able to kill the yeast *Zygosaccharomyces rouxii* within 72 hours. The composition was shown to stable at room temperature for extended periods.

The honeys used in the compositions of the present invention may be identified by their chemical fingerprint. Chemical fingerprinting of honey involves analysing the composition of naturally occurring volatile compounds in multiple samples of species-specific unifloral types of honey. The flavour profile of volatile compounds represents a 'fingerprint' of the honey. The chemical analysis of these volatiles is useful for authenticating the botanical or floral source of honeys, and for identifying components responsible for the strong, distinctive aroma and flavour of honeys. Together with taste flavour compounds such as organic acids, the natural volatiles make up the full flavour of honey. In addition, high-boiling semi-volatiles originating from the floral source are included in the chemical fingerprint of honey. Floral source marker compounds for 14 species-specific unifloral types of honey were identified. A three-step procedure called the Floral Certification Test has been developed. It involves a solvent extraction of volatiles from honey, followed by their detection and quantification using GC and GC-MS, and finally multivariate statistical analysis of the chemical data. These procedures have permitted the identification of numerous compounds that include norisoprenoids, monoterpenes, benzene derivatives, aliphatic compounds, and Maillard reaction products. Methods for the chemical fingerprinting of *Leptospermum scoparium* honey have been disclosed, for example, in WO05/120250. Exemplary honeys for use in the ophthalmic compositions of the present invention are substantially unifloral honeys derived from *Leptospermum scoparium* and *Leptospermum polygalifolium, Leptospermum semibaccatum, Leptospermum semibaccutum, Leptospermum tri-*

*nervium, Leptospermum whitei, Leptospermum speciosum* and *Leptospermum liversidgei*.

In some embodiments, the invention provides a medicinal composition comprising a honey having non-peroxide anti-bacterial activity, wherein the composition comprises from about 19% to about 80% water by weight for use in the treatment of an ophthalmic, nasal or respiratory condition. Examples of ophthalmic conditions include dry eye, conjunctivitis, keratitis, kerato-conjunctivitis, herpes infections, blepharitis, Fuch's dystrophy, Sjogren's syndrome, non-Sjogren's syndrome and acanthmoeba. Examples of suitable respiratory conditions include lung and bronchopulmonary infections including those caused by *Pseudomas aeruginosa, Pneumocystis carinii, Staphylococcus aureus, Haemophilus influenzae, Mycobacterium tuberculosis, Mycobacterium bovis, Mycobacterium africanum, Mycobacterium canetti* and *Mycobacterium microti*; and infections associated with cystic fibrosis, tuberculosis and AIDS, sinusitis, acute rhinitis, atrophic rhinitis, pharyngitis, tonsillitis, laryngitis and bacterial infections of the nasal cavity, for example those due to *Klebsiella ozenae* and nosocomial *S. aureus* bacteraemia due to nasal carrier. Examples of suitable ear conditions include external otitis, acute and chronic otitis media.

In certain embodiments, the invention provides an ophthalmic composition comprising a honey having non-peroxide antibacterial activity, wherein the composition comprises from about 19% to about 80% water by weight for use in the treatment of an ophthalmic condition selected from: chronic corneal oedema associated with Fuchs dystrophy, post operative bullous keratopathy, neurotrophic keratitis, recurrent corneal erosion syndrome corneal abrasions/recurrent erosions, corneal ulcers, corneal oedema, chronic blepharitis, chronic meibomitis with marginal keratitis, tear deficient dry eye, contact lens dry eye, chronic post surgery dry eye, tear deficiency—non autoimmune (non-Sjogrens NSTD), tear deficiency—autoimmune (Sjogren's syndrome SSTD), meibomian gland disease (MGD), tear deficiency and meibomian gland disease, graft vs host disease, blepharitis, bacterial conjunctivitis, marginal conjunctivitis, keratitis, Fuchs dystrophy, canaliculitis (infection associated with using plugs), contact lens epitheliopathy, mucocele and *staphylococcus* blepharitis.

In some embodiments, the invention provides a medicinal composition comprising a honey having non-peroxide anti-bacterial activity, wherein the composition comprises from about 19% to about 80% water by weight is for use in the prophylactic or preventative treatment of an ophthalmic, nasal or respiratory condition.

Generally, the medicinal composition comprises from about 19% to about 80% water by weight, usually from about 20% to 50% by weight, more usually from about 20% to 40% water by weight, typically from about 20% to about 30% water by weight. In specific embodiments, the ophthalmic composition comprises about 21%, 22%, 23%, 24%, 25%, 26%, 27%, 28%, 29%, or 30% water by weight.

The medicinal compositions of the present invention may be used to treat microbial infections of the eye and conditions variously described as dry eye, infections of the respiratory tract, especially the lungs and infections of the ear. The medicinal compositions of the present invention may also be used preventatively to prevent infection occurring, particularly in high risk situations. For example, before surgery, a patient may be administered the compositions of the invention to the nose prior to being taken to theatre to reduce or prevent cross-infection with MESA during surgery.

The microbial infections that may be treated by the methods and medicinal compositions of the present invention may be any opportunistic infection of a wound by a bacterium, or a multiple infection of more than one species of bacteria, fungi, protosoa and/or virus. Common microbial species causing ophthalmic, respiratory and ear infections are known to those skilled in the art.

Microbial species, include fungi, viral, protozoan and bacterial species, causing infections that may be susceptible to treatment by the medicinal compositions of the present invention include: *Aerobacter aerongenes, Aeromonas* spp., *Bacillus* spp., *Bordetella* spp, *Campylobacter* spp., *Chlamydia* spp., *Corynebacterium* spp., *Desulfovibrio* spp., *Escherichia coli*, enteropathogenic, Enterotoxin-producing *E. coli, Helicobacter pylori*, the family herpes viruses (e.g. Herpes simplex, zoster), *Klebsiella pneumoniae, Legionella pneumophiia, Leptospira* spp., *Mycobacterium tuberculosis, M. bovis, Neisseria gonorrhoeae, N. meningitidis, Nocardia* spp., *Proteus mirabilis, P vulgaris, Pseudomonas aeruginosa, Rhodococcus equi, Salmonella enteridis, S. typhimurium, S. typhosa, Shigella sonnei, S. dysenterae, Staphylococcus aureus, S. epidermidis, Streptococcus anginosus, S. inutans, Vibrio cholera, Yersinia pestis, Y. pseudotuberculosis, Actinomycetes* spp., *Streptomyces* spp. Coagulase-negative *Staphylococcus, Propionibacterium* spp, Coliforms, *Haemophilus* spp, *Proteus* spp, *Serratia marcescens, Acinetobacter* spp, *Micrococcus* spp, *Streptococcus viridans, Candida albicans, Aspergillus niger, Enterococcus faecalis*—Vancomycin susceptible, *Enterococcus faecalis*—Vancomycin resistant, *Enterobacter cloacae, Acinetobacter baumanni, Acinetobacter calcoaceticus, Citrobacter freundii, Morganella morganii, Enterococcus faecium, Enterococcus* species, MRSA—Multi-resistant and MRSA—Non multi-resistant.

There are various causes of dry eye syndrome some of which remain unidentified. Dry eye may be treated by administration of artificial tears in order to relieve the subjective symptoms, or by prophylaxis or prevention in order to prevent eyes from drying. There are currently few effective treatments for dry eye syndrome available.

In specific embodiments, the ophthalmic condition in need of treatment by the ophthalmic compositions described herein, is a form of dry eye. In non-limiting examples, the honey compositions of this invention may be used to prevent dry eye, or, if dry eye has occurred, to provide an improved formulation that quickly thereafter ameliorates dry eye and moreover may permit natural tears to operate.

The medicinal compositions disclosed herein may promote goblet cell production, accelerate wound healing, reduce scarring during healing, and reduce the level of scarring already present from previous insult or injury.

The compositions may also be utilised to administer various pharmaceutically active compounds to the eye and/or ear and/or respiratory tract such as the nose and/or lungs. Such pharmaceuticals may include, but are not limited to, anti-hypertensive, anti-glaucoma, neuro-protective, anti-allergy, muco-secretagogue, angiostatic, anti-microbial, and anti-inflammatory agents.

Examples of pharmaceutically active agents which may be included in the compositions of the present invention, and administered via the methods of the present invention include, but are not limited to: glaucoma medication, restasis, plugs, betaxolol, timolol, tetracyclines, pilocarpine, carbonic anhydrase inhibitors and prostaglandins; dopaminergic antagonists; post-surgical antihypertensive agents, such as para-amino clonidine (apraclonidine); anti-infectives, such as ciprofloxacin and tobramycin; non-steroidal and steroidal anti-inflammatories, such as naproxen, diclofenac, suprofen, ketorolac, tetrahydrocortisol and dexamethasone; proteins;

growth factors, such as epidermal growth factor; hyaluronates, anti-allergics, fluticasone, flunisolide, lpratroprium, albuterol and xylometazoline.

For example, in addition to the inherent antimicrobial activity of the medicinal compositions of the present invention, the compositions may also comprise at least one additional antimicrobial agent. The medicinal compositions of the present invention may also be used in conjunction with ophthalmic treatments such as restasis (cyclosporin), or, for example, an agent for the treatment of macular degeneration. Suitably, the combination treatment provides synergism, or at least provides co-therapeutic benefit.

The medicinal compositions may also comprise a surfactant. Suitable surfactants include, but are not limited to: fatty alcohol ethoxylates (alkylpolyethylene glycols); alkylphenol polyethylene glycols; alkyl mercaptan polyethylene glycols; fatty amine ethoxylates (alkylaminopolyethylene glycols); fatty acid ethoxylates (acylpolyethylene glycols); polypropylene glycol ethoxylates (Pluronic); fatty acid alkylolamides (fatty acid amide polyethylene glycols); alkyl polyglycosides, N-alkyl-, N-alkoxypolyhydroxy fatty acid amide, in particular N-methyl-fatty acid glucamide, sucrose esters; sorbitol esters, and esters of sorbitol polyglycol ethers. Preferably, the surfactant selected for application to the eye or nose is mild and does not lead to extensive irritation or promote further tissue damage to the patient.

Subjects may develop acute sensitivity to preservatives contained in ophthalmic compositions. Subjects have been shown to elicit cytoxicity and inflammatory cell responses to some preservatives. For example, use of artificial tears containing preservatives, especially benzalkonium chloride (BAK) and chlorobutanol, may induce irritation in users. Ophthalmic compositions often require frequent instillation, which can further exacerbate problems of sensitivity to preservatives. Whilst preservatives may have effective antimicrobial properties, they may also elicit undesired cytotoxic effects on the corneal epithelium. Punctate epithelial keratitis may be produced both by excessive instillation of preservative-containing ophthalmic composition and by the inability of a dry eye to dilute the preservatives and wash them away from the ocular surface. Moreover, it is a common perception among clinicians that preservatives in tear preparations may cause ocular surface damage. The degree of surface toxicity can range from mild punctate epithelial keratopathy, to severe corneal erosions. Clinical findings indicate that toxic keratoconjunctivitis may be induced by the inappropriate use of preservative-containing artificial tear preparations. (Palmer R M, Kaufman H E; "Tear film, pharmacology of eye drops, and toxicity"; Current Opinion in Ophthalmology 1995; 6; IV: 11-16).

However, preservative activity is desirable for multiple-use ophthalmic compositions. In some instances, large containers, rather than single dose units, are preferred for daily and regular users of ophthalmic compositions. In such regular use cases, preservative activity may, for example, retard the growth of bacteria and increasing shelf life of multiple-use vials. (Perry, H D and Donnenfeld E D; "Issues in the use of preservative-free topicals"; Manag Care 2003; 12 (12 Suppl): 39-41).

The British Pharmacopeia 2005 (BP) states that if a pharmaceutical preparation does not itself have adequate antimicrobial activity, antimicrobial preservatives may be added, particularly to aqueous preparations, to prevent proliferation or to limit microbial contamination which, during normal conditions of storage and use, could occur in a product and present a hazard to the patient from infection and spoilage of the preparation. The BP goes on to state that during development of a pharmaceutical preparation, it should be demonstrated that the antimicrobial activity of the preparation provides adequate protection from adverse effects that may arise from microbial contamination or proliferation during storage and use of the preparation. It is thus desirable that the medicinal compositions of the invention are not readily susceptible to microbial spoilage. An advantage lies herein in that it may not be necessary to add preservatives to the medicinal compositions of the present invention due to their inherent stability. In some embodiments of the present invention, the compositions do not contain added preservatives.

The medicinal compositions of the present invention may contain one or more pharmaceutically acceptable gums in an amount sufficient to increase the viscosity of the composition. The amount of gum required for a particular composition will be determined based on various factors, such as the molecular weight and/or grade of the particular gum selected and the type of gelling properties desired.

The medicinal compositions may contain one or more polysaccharides that may or may not be classed as gums as described above, and may also have other therapeutic properties useful in treating ophthalmic, otic or respiratory disorders. Examples of polysaccharides include but are not limited to: chitosans; chitins; dermatans; hyaluronates; heparans; dermatans, chondroitins, heparins and the like.

The medicinal compositions of the invention may also contain: a tonicity adjusting agent (sodium, potassium or calcium chloride; anhydrous dextrose; polypropylene glycol; glycerol; etc.), a sequestering agent (sodium citrate or the like), a buffering agent (an alkali meal phosphate), chelating agents, solubilisers, pH adjusting agents and/or carriers. Other polymer or monomeric agents such as glycerol may also be added for special processing. Chelating agents may include EDTA and its salts; solubilising agents may include Cremophor ELe and tween 80; other carriers may include amberlite IRP-69; pH adjusting agents may include hydrochloric acid, Tris, triethanolamine and sodium hydroxide. The above listing of examples is given for illustrative purposes and is not intended to be exhaustive. Examples of other agents useful for the purposes of the invention are well known in ophthalmic, nasal and respiratory compositions and are contemplated by the present invention.

The medicinal compositions may contain up to about 1% of one or more viscosity-adjusting agents; up to about 1% of one or more tonicity adjusting agents; usually about 0.3% of one or more buffering agents; and less than 0.1% of a preservative agent.

The ophthalmic compositions of the present invention may be used, in the manufacture of a medicament, to lubricate the eye or provide artificial tear compositions to treat, for example, dry eye. Artificial tear compositions may contain tonicity agents, polymers and polysaccharides as described above.

The ophthalmic compositions according to the present invention may be topically administered to the eye in accordance with techniques well known to persons skilled in the art. For example, the ophthalmic composition may be administered via a conventional bulb-actuated eye dropper. The finished formulations are preferably stored prior to use in opaque or brown containers to protect them from light exposure, and under an inert atmosphere. These compositions can be packaged in preservative-free, single-dose non-reclosable containers. Single use ophthalmic droppers can be sterilised and minimise risk of cross contamination. This permits a single dose of the medicament to be delivered to the eye as a drop, with the container then being discarded after use. Such containers minimise the potential for preservative-related irritation and sensitisation of the corneal epithelium, as has been observed to occur particularly from ophthalmic medicaments containing mercurial preservatives. Multiple dose containers can also be used, if desired, particularly since relatively low viscosities can be obtained in compositions of the invention which permit constant, accurate dosages to be administered dropwise to the eye as many times each day as necessary.

The ophthalmic compositions according to the present invention may also be administered to ocular organs in accordance with other techniques well known to persons skilled in the art, for example: washing, lavage, irrigation, flushing, rinsing and the like. The ophthalmic compositions according to the present invention may, for example, be used to lavage the lachrymal sac.

The ophthalmic compositions according to the present invention may be applied directly or indirectly to the ocular surface or eye lid. The ophthalmic compositions may be used at different phases of treatment, e.g. acute, sub-acute and chronic phase.

Different dosage or treatment regimes may be established for different indications in accordance with methodologies well known to persons skilled in the art. For example, a treatment regime for dry eye may include from about 3 to about 8 drops per eye daily. A treatment regime for the respiratory tract may include about 2 to about 3 sprays per day. A treatment regime for the ear may include 2 to 8 drops in the ear daily.

The ophthalmic compositions of the present invention may be mixed with artificial tear preparations, preferably non-preserved. The ophthalmic compositions of the present invention may be used with both soft and hard contact lenses.

Respiratory compositions of the present invention may also be applied topically to the nose, mouth or throat, for example, by washing, lavage, irrigation, flushing, rinsing, by drops or to the entire or part of the respiratory tract by spray. For example, respiratory compositions may be applied using an atomised spray such as a pump action atomised spray. Such a spray may also be able to deliver an accurate or measured dose of composition.

Otic compositions for application to the ear may also be applied topically to the ear, for example, by washing, lavage, irrigation, flushing, rinsing, syringing or by drops.

EXAMPLES

Example 1.0

Multi-Resistant Clinical Isolates

A challenge set of 130 multi-resistant clinical isolates were specifically selected for use in this study. These organisms comprised 48 strains of MRSA (including both multi-resistant and non-multi resistant phenotypes), 3 strains of vancomycin susceptible *Enterococcus faecalis,* 20 strains of VRE (including both vanA, vanB and vanC phenotypes), 10 ESBL producing isolates of *Escherichia coli,* 12 ESBL positive *Klebsiella pneumoniae,* 6 clinical isolates of *Enterobacter cloacae,* 20 strains of *Pseudomonas aeruginosa* and 11 strains of multi-resistant *Acinetobacter baumanni*. The clinical source and antimicrobial phenotype of test strains is shown in Table 1. Test strains were non-replicate, non-clonal clinical isolates that were cultured from diagnostic specimens submitted to a large tertiary referral hospital in Australia over a 14 year period from 1990 to 2004. All organisms were identified using standard methods in accordance with those outlined in the Manual of Clinical Microbiology. Antimicrobial susceptibility profiles for all staphylococcal and gram negative organisms were determined using the automated Vitek™ system (bioMerieux, R07.1). Enterococcal resistance profiles were determined using CLSI agar dilution protocol (National Committee for Clinical Laboratory Standards. *Methods for Dilution Antimicrobial Susceptibility Tests for Bacteria that grow Aerobically*—Fifth Edition, Standard M7-A5, NCCLS, Villanova, Pa., USA, 2000). Vancomcyin resistance phenotypes were confirmed using genotyping and the species identification confirmed using PCR of specific ddI ligases (Dutka-Malen S, Ever S, Courvalin P., *J Clin Micro,* 1995; 33, 24-27). Clonality of test strains was assessed from pulse field gel electrophoresis profiles obtained using the Genepath™ system (Biorad). Three ATCC type strains were also tested. These included *Staphylococcus aureus* ATCC 25923, *Pseudomonas aeruginosa* ATCC 27853 and *Enterococcus faecalis* ATCC 29212.

Example 1.1

Plate Preparation and Inoculation

Medihoney™, a honey composition having non-peroxide antimicrobial activity derived from *Leptospermum* sp. was serially diluted from 1-20% v/v in Mueller Hinton agar (BBL211438). Control plates containing only Mueller Hinton agar were also prepared. Plates were inoculated on the same day as preparation. Test organisms were subcultured from the −70° C. freezer onto 5% horse blood Colmbia agar (Oxoid CM331) and incubated at 35° C. in ambient air for 18 hours. After this time, a second subculture onto horse blood Columbia agar was then performed. After 18 hours incubation at 35° C., 4-5 colonies of each test isolate were inoculated in 2 mL Tryptone Soy Broth (Oxoid CM129) and incubated at 35° C. in ambient air for 2 hours. Following incubation, the turbidity of each culture was adjusted to a 0.5 McFarland standard. 10 μL of the adjusted suspension was then added to 500 μL of sterile physiological saline in a multi-point inoculator. Mueller Hinton Agar plates containing serial dilutions of Medihoney™ were inoculated using a multipoint inoculation device that delivered an inoculum per plate of approximately $10^4$ cfu/mL. Agar plates were incubated at 35° C. in ambient air for 18 hours. After this time, each plate was examined for the presence of bacterial growth. Complete inhibition of bacterial growth was recorded as no growth. Media showing partial inhibition (shadowing) or 1-2 colonies of test isolates were reported as positive for growth. The comparative $MIC_{50}$ and $MIC_{90}$ values for the different organism types listed above are as shown in Table 2.

TABLE 1

Phenotypic Antimicrobial Resistance Profiles of Clinical Isolates Screened for Susceptibility to Medihoney ™

| Organism | No Strains | Phenotypic Antimicrobial Resistance Profile |
|---|---|---|
| MRSA | | |
| Multi-resistant | 18 | $Pen^R$, $Ox^R$, $Ery^R$, $Gen^R$ |
| Non multi-resistant | 26 | $Pen^R$, $Oxa^R$, $Ery^R$ |
| *Staphylococcus aureus* | | |
| BORSA mecA neg | 2 | $Pen^R$, $Oxa^R$ |
| Multi-resistant mecA neg | 2 | $Pen^R$, $Ery^R$, $Gen^R$ |

TABLE 1-continued

| Phenotypic Antimicrobial Resistance Profiles of Clinical Isolates Screened for Susceptibility to Medihoney ™ | | |
|---|---|---|
| Organism | No Strains | Phenotypic Antimicrobial Resistance Profile |
| ESBL positive strains | | |
| *Escherichia coli* | 2 | $Amp^R$, $SXT^R$, $Gen^R$, $Tob^R$, $Tim^R$, $Cip^R$ |
| | 3 | $Amp^R$, $SXT^R$, $Gen^R$, $Tob^R$, $Tim^R$ |
| | 2 | $Amp^R$, $SXT^R$, $Tim^R$ |
| | 3 | $Amp^R$, $Gent^R$, $Tim^R$ |
| *Klebsiella pneumoniae* | 5 | $Amp^R$, $SXT^R$, $Gen^R$, $Tob^R$, $Tim^R$, $Cip^R$ |
| | 3 | $Amp^R$, $Gen^R$, $Tim^R$ |
| | 4 | $Amp^R$, $SXT^R$, $Gen^R$, $Tim^R$, $Cip^R$ |
| *Enterobacter cloacae* | 1 | $Amp^R$, $SXT^R$, $Gen^R$, $Tob^R$, $Tim^R$, $Cip^R$ |
| | 2 | $Amp^R$, $SXT^R$, $Gen^R$, $Tob^R$, $Tim^R$ |
| | 3 | $Amp^R$, $SXT^R$, $Gen^R$, $Tim^R$, $Cip^R$ |
| *Acinetobacter baumanni* | 3 | $Amp^R$, $Gen^R$, $Tob^R$, $Ak^R$, $Tim^R$, $Cip^R$, $Mem^R$ |
| | 3 | $Amp^R$, $Tim^R$, $Mem^R$ |
| | 4 | $Amp^R$, $Gen^R$, $Tob^R$, $Tim^R$, $Cip^R$, $Mem^R$ |
| | 1 | $Amp^R$, $Gen^R$, $Tim^R$, $Cip^R$, $Mem^R$ |
| *Pseudomonas aeruginosa* | 15 | Fully susceptible |
| | 1 | $Caz^R$, $Tim^R$ |
| | 1 | $Gen^R$ |
| | 2 | $Tim^R$ |
| | 1 | $Cip^R$ |
| *Enterococcus faecalis* | | |
| Vancomycin susceptible | 3 | |
| Vancomycin resistant | | |
| vanA | 1 | $Van^R$, $Tec^R$ |
| vanB | 6 | $Van^R$ |
| *Enterococcus faecium* | | |
| Vancomycin resistant | | |
| vanA | 7 | $Amp^R$, $Van^R$, $Tec^R$ |
| vanB | 4 | $Amp^R$, $Van^R$ |
| *Enterococcus* species | | |
| vanC | 3 | $Van^R$ |

Abbreviations:
Amp - ampicillin,
Caz - cefatzidime,
Cip - ciprofloxacin,
Gen - gentamicin
Mem - meropenem,
Pen - pencillin,
SXT - trimethoprim sulphamethoxazole,
Tec - teicoplanin,
Tim - Ticarcillin clavulanate,
Tob - tobramycin,
Van - vancomycin

TABLE 2

| Comparative $MIC_{50}$ and $MIC_{90}$ Values to Medihoney ™ | | | |
|---|---|---|---|
| Organism (no strains tested) | MIC Range£ | $MIC_{50}$£ | $MIC_{90}$£ |
| MRSA | | | |
| Multi-resistant (18) | 4 | 4 | 4 |
| Non multi-resistant (26) | 4 | 4 | 4 |
| *Staphylococcus aureus* | | | |
| BORSA mecA neg (2) | 4 | 4 | 4 |
| Multi-resistant mecA neg (2) | 4 | 4 | 4 |

TABLE 2-continued

| Comparative $MIC_{50}$ and $MIC_{90}$ Values to Medihoney ™ | | | |
|---|---|---|---|
| Organism (no strains tested) | MIC Range£ | $MIC_{50}$£ | $MIC_{90}$£ |
| ESBL positive strains | | | |
| *Escherichia coli* (10) | 6-8 | 6 | 8 |
| *Klebsiella pneumoniae* (12) | 6-8 | 6 | 6 |
| *Enterobacter cloacae* (6) | 6 | 6 | 6 |
| *Acinetobacter baumanni* (11) | 6-8 | 8 | 8 |
| *Pseudomonas aeruginosa* (20) | 12-14 | 12 | 14 |
| *Enterococcus faecalis* | | | |
| Vancomycin susceptible (3) | 6-8 | 6 | 8 |
| Vancomycin resistant (7) | 6-8 | 8 | 8 |
| *Enterococcus faecium* | | | |
| Vancomycin resistant (11) | 6-8 | 8 | 8 |
| *Enterococcus* species | | | |
| Vancomycin resistant (vanC) (3) | 6 | 6 | 6 |
| ATCC Type Strains | | | |
| *Staphylococcus aureus* ATCC 25923 | 4 | N/A | N/A |
| *Pseudomonas aeruginosa* ATCC 27853 | 8 | N/A | N/A |
| *Enterococcus faecalis* ATCC 29212 | 8 | N/A | N/A |

£data in Table 2 is expressed in terms of volume/volume percentage (v/v) % of honey in water.

Example 2.0

Stability Testing

Samples of honey compositions comprising a honey having non-peroxide antibacterial activity (Medihoney™) with 25% by weight of water and having a water activity of 0.685 referred to as Solution 1 were prepared and stored in opaque polyethylene containers at 25° C.

After 1 year the samples were challenged by *Staphylococcus aureus* inoculum by adding inoculum to a sample and recovering microorganisms from the innoculated sample. A freshly prepared sample that had not been stored was treated under identical conditions as a control sample. The results are shown in Table 3.

A similar test was performed where samples were prepared and stored in polyethylene terephthalate (PET) eye drop containers for varying periods of time and compared with a fresh sample in a polyethylene container and a sample stored for 11 months in a sealed sterile amber glass jar. The inoculum challenge was made as described above with a variety of microbes including *S. aureus, P. aeruginosa, C. albicans, A. niger* and *Z. rouxii*. The results are shown in Table 4.

In a similar trial, test samples were prepared in polyethylene eye drop containers or sealed sterile amber glass jars and stored on an open shelf exposed to ambient light and temperature. A freshly prepared solution was used as a control. The solutions were challenged with a first inoculum followed by a second inoculum of one of *S. aureus, P. aeruginosa, Z. rouxii, A. niger, C. albicans* and *E. faecalis*. The second inoculum was made 14 days after the first inoculum. The results are shown in Table 5.

As can be seen from Tables 3 to 5, each composition of the invention retained its antibacterial activity and was stable under a variety of storage conditions.

TABLE 3

Staphylococcus aureus challenge results

| Product Tested | Age of Product | 1st Inoculum§ | Time 0§ | 24 hours§ | 48 hours | 72 hours§ | 7 days | 28 days§ |
|---|---|---|---|---|---|---|---|---|
| Solution 1 | 1 year | $1.4 \times 10^7$ | $1.1 \times 10^7$ | $8.5 \times 10^5$ | $6.0 \times 10^2$ | <10 | Not tested | Not tested |
| Solution 1 | 1 year | $2.1 \times 10^6$ | $4.5 \times 10^6$ | $8.9 \times 10^5$ | Not tested | Not tested | <10 | <10 |
| Control | 0 months | $2.1 \times 10^7$ | $8.5 \times 10^6$ | Not tested | Not tested | Not tested | <10 | <10 |

§results are displayed in units of "cfu/gram".

TABLE 4

PET Results

| Product Tested | Age of product | Storage Container | Test organisms | 1st inoculum§ | 7 days§ | 14 days§ | 28 days§ |
|---|---|---|---|---|---|---|---|
| Solution 1 | 1 year stability sample | Trial Eye Drops Container | *S. aureus* | $2.1 \times 10^6$ | <10 all | <10 all | <10 all |
| | | | *P. aeruginosa* | $5.0 \times 10^6$ | | | |
| | | | *Candida albicans* | $2.7 \times 10^5$ | | | |
| | | | *Aspergillus niger* | $4.0 \times 10^4$ | | | |
| Solution 1 | 5 months stability sample | Trial Eye Drops Container | *Z. rouxii* | $5.2 \times 10^5$ | <10 all | <10 all | <10 all |
| Solution 1 | Initial stability sample | Trial Eye Drops Container | *S. aureus* | $2.1 \times 10^7$ | <10 all | <10 all | <10 all |
| | | | *P. aeruginosa* | $2.8 \times 10^7$ | | | |
| | | | *Candida albicans* | $1.7 \times 10^6$ | | | |
| | | | *Aspergillus niger* | $1.5 \times 10^5$ | | | |
| Lab Sample 1 | 11 months | Sealed sterile amber glass jar | *Z. rouxii* | $1.4 \times 10^6$ | Not tested | <10 all | <10 all |

§results are displayed in units of "cfu/gram".

TABLE 5

Open Shelf Life Results

| Product Tested | Age of product | Storage Container | Test organisms | 1st inoculum§ | 7 days§ | 14 days§ | 2nd inoculum§ | 21 days§ | 28 days§ |
|---|---|---|---|---|---|---|---|---|---|
| Solution 1 | 1 year | Trial Eye Drops Container | *S. aureus* | $2.1 \times 10^6$ | <10 | <10 | $1.4 \times 10^7$ | <10 | <10 |
| | | | *P. aeruginosa* | $5 \times 10^6$ | <10 | <10 | $2.0 \times 10^7$ | <10 | <10 |
| | | | *Z. rouxii* | $5.2 \times 10^6$ | <10 | <10 | $4.1 \times 10^5$ | <10 | <10 |
| | | | *A. niger* | $4.0 \times 10^6$ | <10 | <10 | $3.6 \times 10^5$ | <10 | <10 |
| | | | *E. Coli* | $5.7 \times 10^6$ | <10 | <10 | $1.9 \times 10^7$ | <10 | <10 |
| Control | 0 Months | Trial Eye Drops Container | *S. aureus* | $2.1 \times 10^7$ | <10 | <10 all | $9.5 \times 10^3$ | <10 all | <10 all |
| | | | *P. aeruginosa* | $2.8 \times 10^7$ | <10 | | $1.8 \times 10^4$ | | |
| | | | *E. faecalis* | $2.5 \times 10^7$ | <10 | | $8.7 \times 10^3$ | | |
| | | | *C albicans* | $1.7 \times 10^6$ | <10 | | $3.6 \times 10^3$ | | |
| | | | *A. niger* | $1.5 \times 10^5$ | 30 | | $1.1 \times 10^4$ | | |
| Lab Sample 1 | 11 Months | Sealed sterile amber glass jar | *S. aureus* | $4.1 \times 10^7$ | <10 | <10 | $6.6 \times 10^3$ | <10 all | <10 all |
| | | | *P. aeruginosa* | $1.3 \times 10^7$ | <10 | <10 | $1.7 \times 10^4$ | | |
| | | | *E. faecalis* | $7.5 \times 10^7$ | <10 | <10 | $9.7 \times 10^4$ | | |
| | | | *C albicans* | $1.5 \times 10^6$ | <10 | <10 | $1.2 \times 10^5$ | | |
| | | | *A. niger* | $3.1 \times 10^5$ | $4.2 \times 10^2$ | 80 | $2.8 \times 10^4$ | | |

§results are displayed in units of "cfu/gram".

Example 3.0

A clinical trial was performed to determine if a solution of honey having non-peroxide antibacterial activity (Medihoney™) referred to as solution 1 is safe and effective adjunct to dry eye treatments in controlling the signs and symptoms of dry eye disease, to verify the antibacterial effects of solution 1 on the ocular surface and to determine the effect of solution 1 on markers of ocular health.

Solution 1 was applied topically to patients suffering from non-Sjogren's tear deficiency (NSTD), Graft vs Host disease (GVHD), Sjogren's syndrome tear deficiency (SSTD), Meibomian gland disease (MGD) which is a form of blepharitis, MGD and NSTD, bacterial conjunctivitis, marginal conjunctivitis, keratitis, neurotrophic keratitis, recurrent erosions, Fuch's dystrophy, Canaliculitis (infection due to a plug), contact lens epitheliopathy, mucocele and *staphylococcus* blepharitis. Application in the form of eye drops was made 3 times per day for 3 months.

The results are given in Table 6 where each column represents the following:

1. numbers of patients with the diagnosis.
2. numbers of patients with the diagnosis indicating improved signs and symptoms during treatment.
3. numbers of patients with the diagnosis indicating improved signs during treatment.
4. numbers of patients with the diagnosis indicating improved symptoms during treatment.
5. numbers of patients with the diagnosis indicating no change in signs or symptoms during treatment.
6. numbers of patients with the diagnosis indicating signs and symptoms were worse during treatment.
7. numbers of patients with the diagnosis with plugs in their eyes during treatment.

8. numbers of patients with the diagnosis with chronic dry eye resulting from surgery.
9. numbers of patients with the diagnosis with ocular atopy.
10. numbers of patients with the diagnosis who were contact lens wearers.
11. numbers of patients with the diagnosis who were also treated with glaucoma medication during treatment.
12. numbers of patients with the diagnosis who were also treated with steroids during treatment.
13. numbers of patients with the diagnosis that stopped treatment before 3 months completed.
14. numbers of patients with the diagnosis with restasis (previous use).
15. numbers of patients with the diagnosis with restasis which was unsuccessful.
16. numbers of patients with the diagnosis with herpes present during treatment.
17. numbers of patients with the diagnosis who were also treated with antibiotics during treatment.
18. numbers of patients with the diagnosis who suffered an adverse effect.
19. description of the adverse effect.

As can be seen from Table 6, many of the patients showed improvements in signs and/or symptoms during and after treatment.

TABLE 6

Clinical data relating to patient treatment with Solution 1

| Diagnosis | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| NSTD | 47 | 24 | 3 | 3 | 16 | 1 | 19 | 7 | 1 | 4 | 7 | 9 | 2 | 6 | 5 | 1 | 1 | 1 | Discontinued visits before review. Dropout. 1 mth. No change. Stinging. |
| GVHD | 5 | 4 | 0 | 0 | 1 | 0 | 1 | 0 | 0 | 0 | 0 | 3 | 0 | 1 | 1 | 0 | 0 | 0 | |
| SSTD | 11 | 6 | 0 | 0 | 5 | 0 | 3 | 0 | 0 | 1 | 0 | 2 | 0 | 0 | | 1 | 1 | 0 | |
| MGD | 28 | 18 | 0 | 1 | 9 | 0 | 0 | 0 | 3 | 2 | 0 | 10 | 4 | 0 | | 1 | 2 | 1 | 3 mths; no change. Excessive stinging, burning, itching. Ocular atopy. Steroids. |
| MGD + NSTD | 22 | 14 | 2 | 0 | 4 | 2 | 6 | 3 | 1 | 1 | 0 | 3 | 0 | 0 | | 2 | 0 | 2 | 1 - excessive stinging, no change, 1 mth. 2 - excessive stinging, burning, redness? Allergy. 2 mths, worse |
| Bacterial conjunctivitis | 4 | 3 | 0 | 0 | 1 | 0 | 0 | 0 | 0 | 0 | 0 | 0 | 0 | 0 | | 0 | 0 | 0 | |
| Marginal conjunctivitis | 1 | 1 | 0 | 0 | 0 | 0 | 0 | 0 | 0 | 0 | 0 | 0 | 0 | 0 | | 0 | 0 | 0 | |
| Keratitis | 0 | 0 | 0 | 0 | 0 | 0 | 0 | 0 | 0 | 0 | 0 | 0 | 0 | 0 | | 0 | 0 | 0 | |
| Neurotrophic keratitis | 2 | 2 | 0 | 0 | 0 | 0 | 0 | 0 | 0 | 0 | 0 | 0 | 0 | 0 | | 0 | 0 | 0 | |
| Recurrent erosions | 7 | 4 | 1 | 0 | 2 | 0 | 1 | 1 | 1 | 0 | 0 | 1 | 1 | 0 | | 0 | 0 | 1 | ?allergy, no change; 2 mths, ocular atopy |
| Fuchs dystrophy | 3 | 0 | 0 | 0 | 3 | 0 | 0 | 0 | 0 | 0 | 2 | 0 | 0 | 0 | | 0 | 0 | 0 | |
| Canaliculitis | 2 | 1 | 0 | 0 | 1 | 0 | 0 | 0 | 0 | 0 | 0 | 0 | 0 | 0 | | 0 | 0 | 0 | |
| Contact lens epitheliopathy | 7 | 5 | 0 | 0 | 2 | 0 | 0 | 0 | 1 | 6 | 0 | 2 | 0 | 0 | | 0 | 0 | 0 | |
| Mucocele | 1 | 1 | 0 | 0 | 0 | 0 | 0 | 0 | 0 | 0 | 0 | 1 | 0 | 0 | | 0 | 1 | 0 | |
| *Staphylococcus* blepharitis | 0 | 0 | 0 | 0 | 0 | 0 | 0 | 0 | 0 | 0 | 0 | 0 | 0 | 0 | | 0 | 0 | 0 | |

Example 4.0

Commentary on Clinical Responses 4.1 Whitening of the Eye

Red eyes are typically caused by enlarged, dilated blood vessels leading to the appearance of redness on the surface of the eye. Patients have reported a dramatic whitening of the eye following application of Solution 1.

4.2 Improved Goblet Cell Density

In conjunctiva, goblet cells are responsible for secreting the gel-forming mucin. Goblet cell density is a good indicator in the diagnosis of ocular surface diseases. The use of Solution 1 in the clinical trial showed an increase in goblet cell density. This is an indicator of an improvement in the ocular surface.

4.3 Chemotactic Agent

Eye drop application of Solution 1 created a white cell response when applied ½ hour prior to refractive surgery. White blood cells (T cells) were observed to rush into the corneal surface. The white blood cells were observed under a slit lamp.

4.4 Blockage of Lacrimal Sac

Lacrimal sac was blocked and micro-organisms (germs) starting to increase. A 2:1 (Solution 1:distilled water) dilution of Solution 1, was put into syringe and the lacrimal sac was lavaged out by syringing the solution into the sac. This promoted healing and decreased the amount of micro-organisms (germs).

4.5 Resolution of Stimulus to Scar Formation

The application of eye drops of Solution 1 helped to stop the occurrence of ocular scarring and allowed normal healing to continue. The solution was observed to help mitigate development of scar tissue and also reduces the amount of existing scar tissue.

4.6 Vision Improvement

Sight returns with reduction of oedema of the eye created by the application of eye drops of Solution 1.

The claims defining the invention are as follows:

1. A method of treating a microbial based ophthalmic condition in a subject, the method comprising administering to the subject a therapeutically effective amount of a medicinal composition comprising a filtered honey having non-peroxide antibacterial activity, wherein the honey is substantially derived from a *Leptospermum* species;

wherein the honey has been filtered to exclude particles with a diameter of greater than about 25 microns;

wherein the filtered honey does not undergo yeast fermentation normally associated with honey at moisture contents greater than 19% water by weight; and wherein the composition comprises at least 19% and less than 30% water by weight and has a water activity of about 0.63 to about 0.85; and wherein the ophthalmic condition is selected from the group consisting of chronic corneal oedema associated with Fuchs dystrophy, post operative bullous keratopathy, neurotrophic keratitis, recurrent corneal erosion syndrome corneal abrasions/recurrent erosions, corneal ulcers, corneal oedema, chronic blepharitis, chronic meibomitis with marginal keratitis, tear deficient dry eye, contact lens dry eye, chronic post surgery dry eye, tear deficiency—non autoimmune (non-Sjogrens NSTD), tear deficiency—autoimmune (Sjogren's syndrome SSTD), meibomian gland disease (MGD), tear deficiency and meibomian gland disease, graft vs host disease, blepharitis, bacterial conjunctivitis, marginal conjunctivitis, keratitis, Fuchs dystrophy, canaliculitis (infection associated with using plugs), contact lens epitheliopathy, mucocele and *staphylococcus blepharitis*.

2. The method of claim 1, wherein the composition comprises between 19% and less than 27% water by weight.

3. The method of claim 1, wherein the composition comprises about 25% water by weight.

4. The method of claim 1 wherein the microbial based ophthalmic condition is a bacterial infection.

5. The method of claim 1, further comprising treatment with another pharmaceutical agent for treating an ophthalmic, respiratory or ear condition.

6. The method of claim 1, wherein the honey is substantially derived from *Leptospermum scoparium*.

7. The method of claim 1, wherein the composition further comprises at least one tonicity adjusting agent.

8. The method of claim 1, wherein the composition further comprises one or more compounds selected from the group consisting of: a surfactant, a viscosity adjusting agent, a buffering agent, a preservative agent, and a combination thereof.

9. The method of claim 1, wherein said administering comprises one or more of the administration forms selected from the group consisting of: washing, lavage, irrigation, flushing, rinsing, drops, and a spray.

10. The method of claim 1, wherein said honey has been filtered to exclude particles with a diameter of greater than about 10 microns.

11. The method of claim 1, wherein said honey has been filtered to exclude particles with a diameter of greater than about 5 microns.

12. A method of treating a microbial infection in a subject, the method comprising administering to the subject a therapeutically effective amount of a medicinal composition comprising a filtered honey having non-peroxide antibacterial activity, wherein the honey is substantially derived from a *Leptospermum* species;

wherein the honey has been filtered to exclude particles with a diameter of greater than about 25 microns;

wherein the filtered honey does not undergo yeast fermentation normally associated with honey at moisture contents greater than 19% water by weight; and wherein the composition comprises at least 19% and less than 30% water by weight and has a water activity of about 0.63 to about 0.85; and wherein the microbial infection is caused by a microbial species selected from the group consisting of: *Staphylococcus aureus, Escherichia coli, Klebsiella pneumoniae, Enterobacter cloacae, Acinetobacter baumanni, Pseudomonas aeruginosa, Enterococcus faecalis*, and *Enterococcus faecium*.

13. A method of treating a microbial based respiratory condition in a subject, the method comprising administering to the subject a therapeutically effective amount of a medicinal composition comprising a filtered honey having non-peroxide antibacterial activity, wherein the honey is substantially derived from a *Leptospermum* species;

wherein the honey does not comprise particles with a diameter of greater than about 25 microns;

wherein the filtered honey does not undergo yeast fermentation normally associated with honey at moisture contents greater than 19% water by weight; and wherein the composition comprises at least 19% and less than 30% water by weight and has a water activity of about 0.63 to about 0.85; and wherein the respiratory condition is a bacterial based condition selected from the group consisting of a lung or bronchopulmonary infection, an infection associated with cystic fibrosis, tuberculosis or AIDS, pneumonia, acute bacterial bronchitis, common cold, sinusitis, acute rhinitis, atrophic rhinitis, pharyngitis, tonsillitis, laryngitis and a bacterial infection of the nasal cavity.

14. A method of treating a microbial based ear condition in a subject, the method comprising administering to the subject a therapeutically effective amount of a medicinal composition comprising a filtered honey having non-peroxide antibacterial activity, wherein the honey is substantially derived from a *Leptospermum* species;

wherein the honey does not comprise particles with a diameter of greater than about 25 microns;

wherein the filtered honey does not undergo yeast fermentation normally associated with honey at moisture contents greater than 19% water by weight; and wherein the composition comprises at least 19% and less than 30% water by weight and has a water activity of about 0.63 to about 0.85; and wherein the ear condition is bacterial based external otitis, acute or chronic otitis media.

* * * * *

UNITED STATES PATENT AND TRADEMARK OFFICE

CERTIFICATE OF CORRECTION

PATENT NO. : 8,568,790 B2
APPLICATION NO. : 12/301931
DATED : October 29, 2013
INVENTOR(S) : Anthony Peter Moloney It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 957 days.

Signed and Sealed this
Fifteenth Day of September, 2015

Michelle K. Lee
*Director of the United States Patent and Trademark Office*